(12) United States Patent
Li et al.

(10) Patent No.: US 12,011,617 B2
(45) Date of Patent: Jun. 18, 2024

(54) METHOD, DEVICE, AND SYSTEM FOR DETECTING INSTALLATION OF COLLIMATOR OF RADIOTHERAPY EQUIPMENT

(71) Applicant: SHENZHEN OUR NEW MEDICAL TECHNOLOGIES DEVELOPMENT CO., LTD., Shenzhen (CN)

(72) Inventors: Jinsheng Li, Shenzhen (CN); Hao Yan, Xi'an (CN)

(73) Assignee: Shenzhen Our New Medical Technologies Development Co., Ltd., Shenzhen (CN)

( * ) Notice: Subject to any disclaimer, the term of this patent is extended or adjusted under 35 U.S.C. 154(b) by 830 days.

(21) Appl. No.: 17/259,905

(22) PCT Filed: Jul. 12, 2018

(86) PCT No.: PCT/CN2018/095471
§ 371 (c)(1),
(2) Date: Jan. 12, 2021

(87) PCT Pub. No.: WO2020/010583
PCT Pub. Date: Jan. 16, 2020

(65) Prior Publication Data
US 2021/0290980 A1    Sep. 23, 2021

(51) Int. Cl.
*A61N 5/10* (2006.01)
(52) U.S. Cl.
CPC ......... *A61N 5/1075* (2013.01); *A61N 5/1045* (2013.01); *A61N 5/1065* (2013.01)

(58) Field of Classification Search
CPC .. A61N 5/1075; A61N 5/1045; A61N 5/1065; A61N 5/1048
See application file for complete search history.

(56) References Cited

U.S. PATENT DOCUMENTS

2015/0352376 A1*   12/2015   Wiggers ............... A61B 6/06
378/207

FOREIGN PATENT DOCUMENTS

| CN | 101209367 A | 7/2008 |
|---|---|---|
| CN | 101209368 A | 7/2008 |
| CN | 101969852 A | 2/2011 |
| CN | 102526885 A | 7/2012 |
| CN | 102554704 A | 7/2012 |

(Continued)

OTHER PUBLICATIONS

International search report of PCT application No. PCT/CN2018/095471 dated Apr. 3, 2019.

(Continued)

*Primary Examiner* — Courtney D Thomas
(74) *Attorney, Agent, or Firm* — Knobbe, Martens, Olson & Bear LLP

(57) ABSTRACT

Disclosed is a method for detecting installation of a collimator of radiotherapy equipment. The method includes: acquiring a projection to be detected of a beam passing through the collimator and an isocentric plane of the radiotherapy equipment in sequence on a ray detector; comparing the projection to be inspected with a reference projection, and determining an installation deviation of the collimator of the radiotherapy equipment based on a deviation between the projection to be detected and the reference projection.

20 Claims, 7 Drawing Sheets

(56) References Cited

FOREIGN PATENT DOCUMENTS

| | | |
|---|---|---|
| CN | 202844376 U | 4/2013 |
| CN | 106126767 A | 11/2016 |
| CN | 107198832 A | 9/2017 |
| JP | 2016152992 A | 8/2016 |

OTHER PUBLICATIONS

First office action of Chinese application No. 201880005153.1 dated Dec. 28, 2020.

* cited by examiner

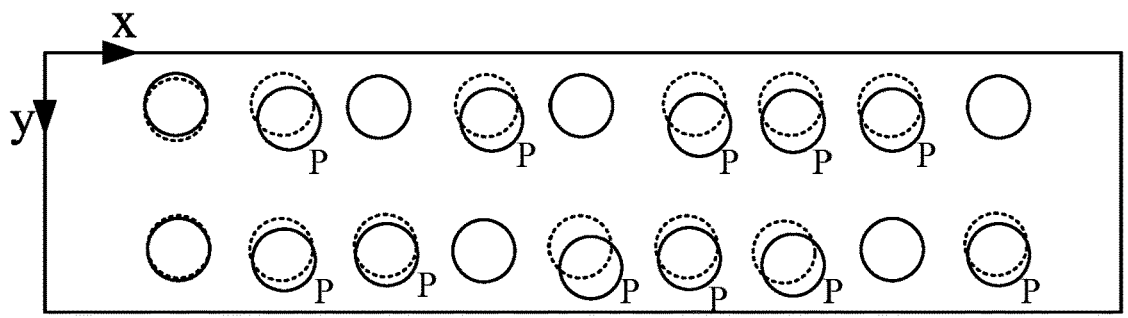

FIG. 6

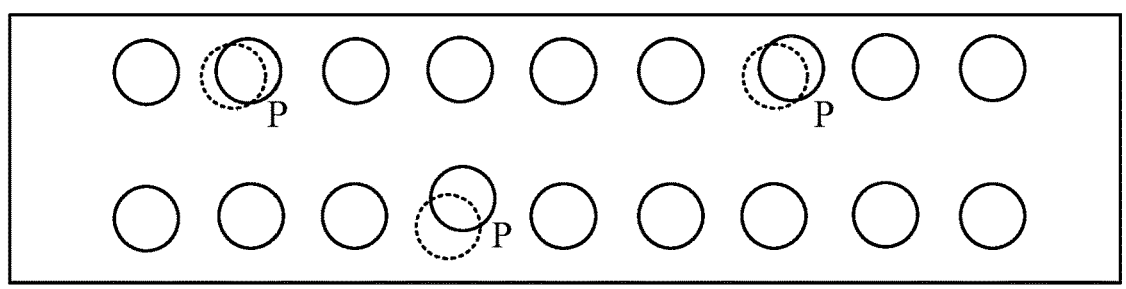

FIG. 7

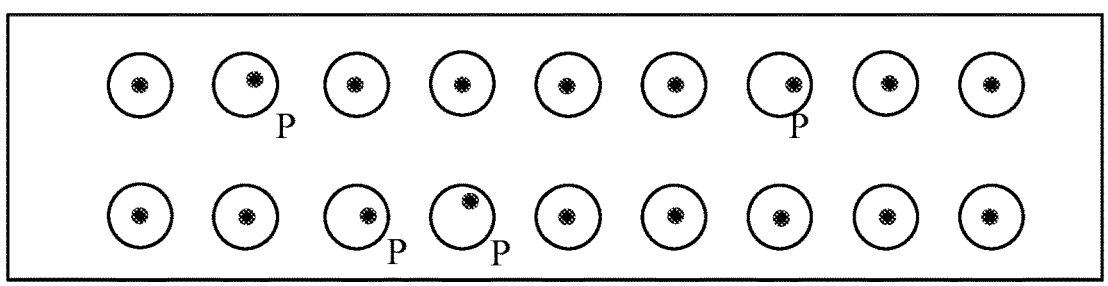

FIG. 8

| Acquiring the projections to be detected of beams passing through a collimator and an isocentric plane of radiotherapy equipment in sequence when a gantry of the radiotherapy equipment is rotated at different rotation angles on a ray detector | 901 |
|---|---|

| Determining an installation stability of the collimator of the radiotherapy equipment by comparing the projections to be detected acquired at the different rotation angles | 902 |
|---|---|

FIG. 9 a deviation value between the geometric center of the projection to be detected and the geometric center of the reference projection.

METHOD, DEVICE, AND SYSTEM FOR DETECTING INSTALLATION OF COLLIMATOR OF RADIOTHERAPY EQUIPMENT

This application is a US National Phase application of International Application No. PCT/CN2018/095471 filed on Jul. 12, 2018, the contents of which are incorporated by reference herein in their entireties.

TECHNICAL FIELD

The present disclosure relates to the field of mechanical equipment, and in particular, relates to a method, device, and system for detecting installation of a collimator of radiotherapy equipment.

BACKGROUND

In modern medicine, radiotherapy is an important means of treating malignant tumors. The radiotherapy refers to killing the tumors using high-energy rays. Currently, radiotherapy is mainly carried out by radiotherapy equipment. The radiotherapy equipment generally includes a radiation source and a collimator. The radiation source is configured to emit the rays, and the collimator is configured to generate a radiation field that meets the requirements. The radiation field defines an irradiation range of the rays. The rays emitted by the radiation source form a beam after passing through the radiation field generated by the collimator and irradiate a tumor lesion area. However, the installation accuracy of the collimator often directly affects a therapeutic effect of the radiotherapy equipment.

SUMMARY

Embodiments of the present disclosure provide a method, device, and system for detecting installation of a collimator of radiotherapy equipment, which can solve the problems in the related art that the film is manually installed, the installation is cumbersome, the manual installation operation easily affects the detection accuracy and ultimately affects the installation accuracy of the collimator, and thus the position adjustment operation is relatively complicated. The technical solutions are as follows.

According to a first aspect of the embodiments of the present disclosure, a method for detecting installation of a collimator of radiotherapy equipment is provided. The method includes:

acquiring a projection to be detected of a beam passing through the collimator and an isocentric plane of the radiotherapy equipment in sequence on a ray detector; and comparing the projection to be detected with a reference projection, and determining an installation deviation of the collimator of the radiotherapy equipment based on a deviation between the projection to be detected and the reference projection.

Optionally, said comparing the projection to be detected with the reference projection, and determining the installation deviation of the collimator of the radiotherapy equipment based on the deviation between the projection to be detected and the reference projection includes:

respectively determining a geometric center of the projection to be detected and a geometric center of the reference projection; and determining the installation deviation of the collimator of the radiotherapy equipment based on a deviation between the geometric center of the projection to be detected and the geometric center of the reference projection.

Optionally, the reference projection is a preset projection of the collimator or a projection of a metal ball disposed in an isocenter of the radiotherapy equipment.

Optionally, the radiotherapy equipment is focusing radiotherapy equipment with a plurality of collimators; and said comparing the projection to be detected with the reference projection, and determining the installation deviation of the collimator of the radiotherapy equipment based on the deviation between the projection to be detected and the reference projection includes:

in a preset coordinate system, in the case that the deviations between geometric centers of a first number of projections to be detected and geometric centers of corresponding reference projections are not less than a preset deviation, and the deviations are the same in terms of direction, determining that the plurality of collimators have a system installation deviation, the first number being greater than or equal to a preset number; and determining the system installation deviation based on the deviation between the geometric center of each of the projections to be detected and the geometric center of the corresponding reference projection.

Optionally, after determining the system installation deviation, the method further includes:

in the case that deviations between geometric centers of a second number of projections to be detected and geometric centers of corresponding reference projections are not less than the preset deviation, determining that each collimator of the second number of collimators has an installation deviation, the second number being less than the preset number; and determining an installation deviation of a corresponding collimator based on the deviation between the geometric center of each of the projections to be detected in the second number of projections to be detected and the geometric center of the corresponding reference projection.

Optionally, the preset coordinate system is a two-dimensional coordinate system having an x-axis and a y-axis perpendicular to each other; and after acquiring the projection to be detected of the beam passing through the collimator and the isocentric plane of the radiotherapy equipment in sequence on the ray detector, the method further includes:

in the case that an absolute value of a difference between coordinates of the geometric center of the projection to be detected and coordinates of the geometric center of the corresponding reference projection in an x-axis direction is not less than a first preset deviation value, and/or, in the case that an absolute value of a difference between the coordinates of the geometric center of the projection to be detected and the coordinates of the geometric center of the corresponding reference projection in a y-axis direction is not less than a second preset deviation value, determining that the deviation between the geometric center of the projection to be detected and the geometric center of the corresponding reference projection is not less than the preset deviation.

Optionally, the plurality of collimators are disposed in a collimation body; and after determining the system installation deviation, the method further includes:

adjusting an overall installation position of the plurality of collimators by adjusting a position of the collimation body based on the system installation deviation; and after determining the installation deviation of the corresponding collimator, the method further includes:

adjusting an installation position of the collimator based on the installation deviation of the collimator.

According to a second aspect of the embodiments of the present disclosure, a method for detecting installation of a collimator of radiotherapy equipment is provided. The method includes:

acquiring projections to be detected of beams passing through the collimator and an isocentric plane of the radiotherapy equipment in sequence on a ray detector when a gantry of the radiotherapy equipment is rotated at different rotation angles; and determining an installation stability of the collimator of the radiotherapy equipment by comparing the projections to be detected acquired at the different rotation angles.

Optionally, said determining the installation stability of the collimator of the radiotherapy equipment by comparing the projections to be detected acquired at the different rotation angles includes:

comparing shapes and positions of the projections to be detected acquired at the different rotation angles; and determining that the collimator is stably installed in the case that the shapes and positions of the projections to be detected acquired at the different rotation angles are the same.

According to a third aspect of the embodiments of the present disclosure, an apparatus for detecting installation of a collimator of radiotherapy equipment is provided. The apparatus includes:

an acquiring module, configured to acquire a projection to be detected of a beam passing through the collimator and an isocentric plane of the radiotherapy equipment in sequence on a ray detector; and a determining module, configured to compare the projection to be detected with a reference projection, and determine an installation deviation of the collimator of the radiotherapy equipment based on a deviation between the projection to be detected and the reference projection.

According to a fourth aspect of the embodiments of the present disclosure, a device for detecting installation of a collimator of radiotherapy equipment is provided. The device includes a memory, a processor, and a computer program stored in the memory and capable of running on the processor, wherein the processor, when executing the computer program, is caused to perform the steps of the method according to the first aspect.

According to a fifth aspect of the embodiments of the present disclosure, a computer-readable storage medium is provided. The storage medium stores a computer program, wherein the computer program, when executed by a processor, causes the processor to perform the steps of the method according to the first aspect.

According to a sixth aspect of the embodiments of the present disclosure, a computer program product is provided. The computer program product stores instructions therein, wherein the computer program product, when running on a computer, causes the computer to perform the steps of the method according to the first aspect.

According to a seventh aspect of the embodiments of the present disclosure, an apparatus for detecting installation of a collimator of radiotherapy equipment is provided. The apparatus includes:

an acquiring module, configured to acquire projections to be detected of beams passing through the collimator and an isocentric plane of the radiotherapy equipment in sequence on a ray detector when a gantry of the radiotherapy equipment is rotated at different rotation angles; and a determining module, configured to determine an installation stability of the collimator of the radiotherapy equipment by comparing the projections to be detected acquired at the different rotation angles.

According to an eighth aspect of the embodiments of the present disclosure, a device for detecting installation of a collimator of radiotherapy equipment is provided. The device includes a memory, a processor, and a computer program stored in the memory and capable of running on the processor, wherein the processor, when executing the computer program, is caused to perform the steps of the method according to the second aspect.

According to a ninth aspect of the embodiments of the present disclosure, a computer-readable storage medium is provided. The storage medium stores a computer program, wherein the computer program, when executed by a processor, causes the processor to perform the steps of the method according to the second aspect.

According to a tenth aspect of the embodiments of the present disclosure, a computer program product is provided. The computer program product stores instructions therein, wherein the computer program product, when running on a computer, causes the computer to perform the steps of the method according to the second aspect.

According to an eleventh aspect of the embodiments of the present disclosure, a system for detecting installation of a collimator of radiotherapy equipment is provided. The system includes: the radiotherapy equipment, a ray detector, and a processing component.

A beam passing through the collimator and an isocentric plane of the radiotherapy equipment in sequence forms a projection to be detected on the ray detector.

The processing component includes the apparatus for detecting the installation of the collimator of the radiotherapy equipment according to the third aspect or includes the device for detecting the installation of the collimator of the radiotherapy equipment according to the fourth aspect.

Optionally, the processing component further includes the apparatus for detecting the installation of the collimator of the radiotherapy equipment according to the seventh aspect or includes the device for detecting the installation of the collimator of the radiotherapy equipment according to the eighth aspect.

BRIEF DESCRIPTION OF THE DRAWINGS

For clear descriptions the technical solutions in the embodiments of the present disclosure, the following briefly introduces the accompanying drawings required for describing the embodiments. Apparently, the accompanying drawings in the following description show merely some embodiments of the present disclosure, and a person of ordinary skill in the art may still derive other drawings from these accompanying drawings without creative efforts.

FIG. 6 is a schematic diagram of projections to be detected and corresponding reference projections according to an embodiment of the present disclosure;

FIG. 7 is a schematic diagram of projections to be detected and corresponding reference projections according to an embodiment of the present disclosure;

FIG. 8 is a schematic diagram of projections to be detected and corresponding reference projections according to an embodiment of the present disclosure;

FIG. 9 is a flowchart of still a further method for detecting installation of a collimator of radiotherapy equipment according to an embodiment of the present disclosure;

DETAILED DESCRIPTION

The present disclosure is described in further detail with reference to the accompanying drawings, to present the objects, technical solutions, and advantages of the present disclosure more clearly. It is obvious that the described embodiments are only part but not all of the embodiments of the present disclosure. All other embodiments acquired by those skilled in the art without creative efforts based on the embodiments in the present disclosure are within the protection scope of the present disclosure.

In the related art, an installation deviation of the collimator is usually detected by adopting a film. In the case that the installation deviation does not meet the requirements, an installation position of the collimator needs to be adjusted. Specifically, whether a projection center of the beam formed by the rays emitted from the radiation source after passing through the collimator on the film on an isocentric plane is located at a preset position on the film is detected. In the case that the projection center is located at the preset position, it is determined that the installation deviation of the collimator meets the requirements. In the case that the projection center is not located at the preset position, it is determined that the installation deviation of the collimator does not meet the requirements, and then the installation position of the collimator is adjusted.

Before the installation deviation of the collimator is detected by adopting the film, the film needs to be manually installed, the installation is cumbersome, the manual installation operation easily affects the detection accuracy and ultimately affects the installation accuracy of the collimator, and thus the position adjustment operation is relatively complicated. In addition, since the film is disposed in an isocentric position, the installation accuracy of a single collimator cannot be reflected.

Figure 1:
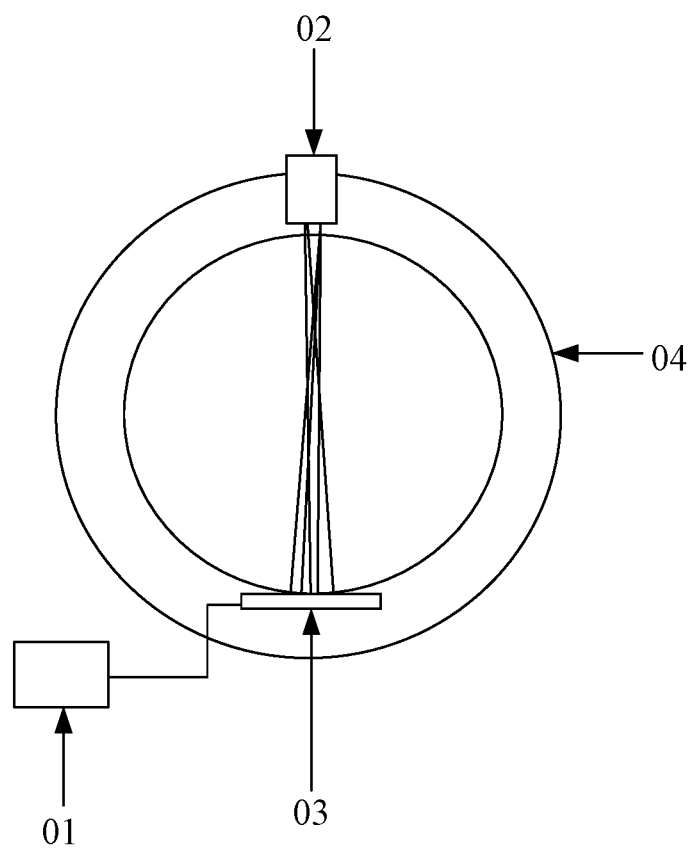
FIG. 1 is a schematic diagram of an implementation environment involved in an embodiment of the present disclosure.

Referring to FIG. 1, a schematic diagram of an implementation environment involved in an embodiment of the present disclosure is shown. The implementation environment may include a processing component 01, a radiotherapy equipment treatment head 02 and a ray detector 03. The treatment head 02 includes at least one radiation source. Each radiation source is correspondingly provided with a collimator, and the treatment head 02 is disposed on a gantry 04, and may rotate along with the gantry 04.

The radiotherapy equipment may be focusing radiotherapy equipment with a plurality of collimators, or conformal intensity-modulated radiotherapy equipment with a multi-leaf collimator. The embodiment of the present disclosure does not limit the type of the radiotherapy equipment.

Exemplarily, the gantry may be a drum-type gantry, and may also be a C-shaped arm gantry, a cantilever type gantry, a semi-arc gantry, or the like. The radiation source may be an accelerator radiation source (generally an X-ray source) or an isotope radiation source (generally a cobalt source).

The radioactive source is configured to emit rays, the collimator is configured to generate a radiation field that meets the requirements, and the rays emitted by the radiation source pass through the radiation field generated by the collimator to form a beam. In the embodiment of the present disclosure, the beam passing through the collimator and an isocentric plane of the radiotherapy equipment in sequence forms a projection to be detected on the ray detector. The embodiment of the present disclosure compares the projection to be detected with a reference projection. Specifically, an installation deviation of the collimator of the radiotherapy equipment is determined by comparing the positions of the projection to be detected and the reference projection on the ray detector. The isocentric plane refers to a plane passing through an isocenter and perpendicular to a connecting line between the radiotherapy equipment and the detector.

In the embodiment of the present disclosure, the reference projection may be acquired in various ways. For example, the reference projection may be a preset projection of the collimator. For another example, the reference projection may be a projection of a metal ball disposed in the isocenter of the radiotherapy equipment. For example, the metal ball may be a tungsten ball.

Figure 2:
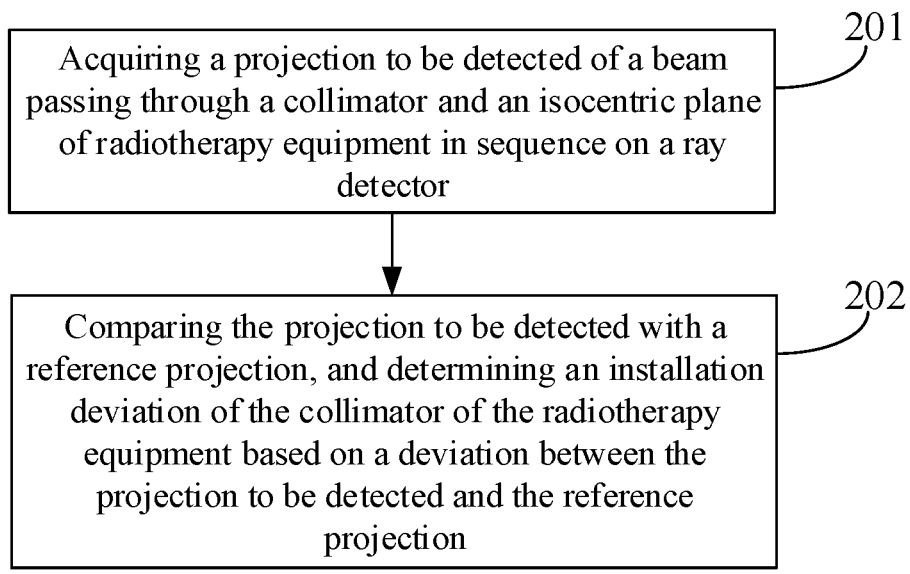
FIG. 2 is a flowchart of a method for detecting installation of a collimator of radiotherapy equipment according to an embodiment of the present disclosure.

Referring to FIG. 2, a flowchart of a method for detecting installation of a collimator of radiotherapy equipment according to an embodiment of the present disclosure is shown. The method may be configured for the processing component 01 in the implementation environment shown in FIG. 1. The method is employed to detect the installation deviation of the collimator of the radiotherapy equipment. As shown in FIG. 2, the method may include the following steps:

In 201, a projection to be detected of a beam passing through the collimator and an isocentric plane of the radiotherapy equipment in sequence on a ray detector is acquired.

The isocentric plane refers to a plane passing through an isocenter and perpendicular to a connecting line between the radiotherapy equipment and the detector.

In 202, the projection to be detected is compared with a reference projection, and the installation deviation of the collimator of the radiotherapy equipment is determined based on a deviation between the projection to be detected and the reference projection.

Specifically, comparing the projection to be detected with the reference projection includes comparing the positions of the projection to be detected with the reference projection on the ray detector. In this step, the positions of the projection to be detected and the reference projection on the ray detector are compared, and the installation deviation of the collimator of the radiotherapy equipment is determined based on the deviation between the positions of the projection to be detected and the reference projection on the ray detector.

In summary, in the method for detecting the installation of the collimator of the radiotherapy equipment according to the embodiment of the present disclosure, the projection to be detected of the beam passing through the collimator and the isocentric plane of the radiotherapy equipment in sequence on the ray detector is acquired, the projection to be detected is compared with the reference projection, and the installation deviation of the collimator of the radiotherapy equipment is determined based on the deviation between the projection to be detected and the reference projection. There is no need to manually install the film, such that the operation of detecting the installation deviation of the collimator is simplified. Therefore, the operation of adjusting the installation position of the collimator is simplified and the detection accuracy is improved. Meanwhile, the amount of radiation to installation persons is also reduced, and the impact on the health of the installation persons is further mitigated.

Figure 3:
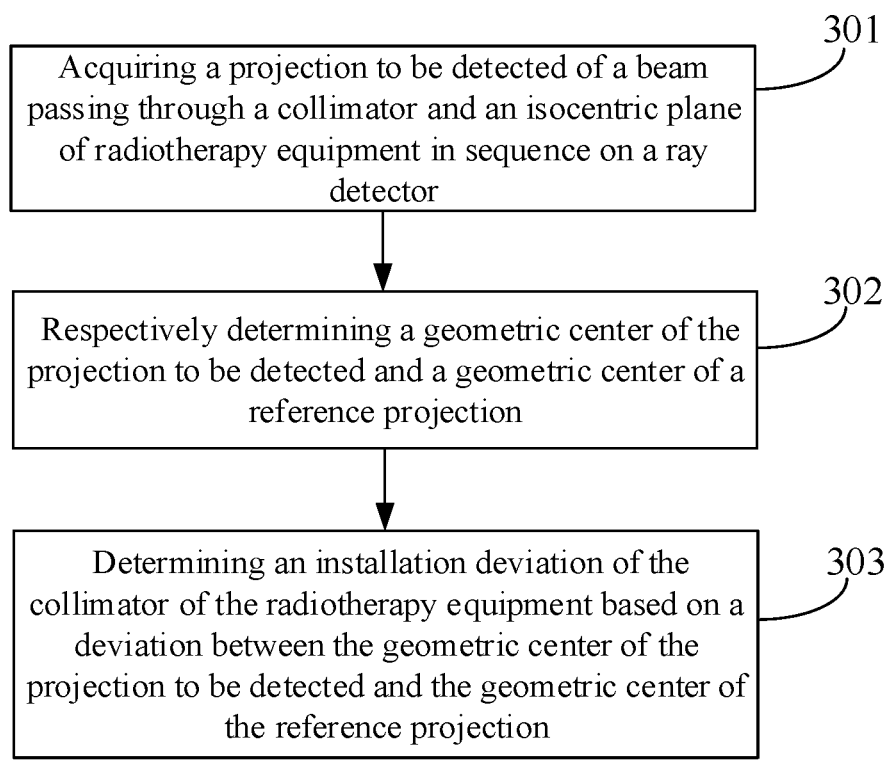
FIG. 3 is a flowchart of another method for detecting installation of a collimator of radiotherapy equipment according to an embodiment of the present disclosure.

Referring to FIG. 3, a flowchart of another method for detecting installation of a collimator of radiotherapy equipment according to an embodiment of the present disclosure is shown. The method may be configured for the processing component 01 in the implementation environment shown in FIG. The method is employed to detect the installation deviation of the collimator of the radiotherapy equipment. As shown in FIG. 3, the method may include the following steps:

In 301, a projection to be detected of a beam passing through the collimator and an isocentric plane of the radiotherapy equipment in sequence on a ray detector is acquired.

In 302, a geometric center of the projection to be detected and a geometric center of the reference projection are respectively determined.

In 303, based on a deviation between the geometric center of the projection to be detected and the geometric center of the reference projection, the installation deviation of the collimator of the radiotherapy equipment is determined.

Exemplarily, when the radiotherapy device is a conformal intensity-modulated radiotherapy device with a multi-leaf collimator, the processing component may firstly acquire the projection to be detected of the beam passing through the collimator and the isocentric plane of the radiotherapy device in sequence on the ray detector, then determine the geometric center of the projection to be detected and the geometric center of the reference projection, and then determine the installation deviation of the multi-leaf collimator based on the deviation between the geometric center of the projection to be detected and the geometric center of the reference projection. For example, when the deviation between the geometric center of the projection to be detected and the geometric center of the reference projection is not less than the preset deviation, the installation position of the multi-leaf collimator may be adjusted, such that the installation position of the multi-leaf collimator meets installation requirements.

In summary, in the method for detecting the installation of the collimator of the radiotherapy equipment according to the embodiment of the present disclosure, the projection to be detected of the beam passing through the collimator and the isocentric plane of the radiotherapy equipment in sequence on the ray detector is acquired, the projection to be detected is compared with the reference projection, and the installation deviation of the collimator of the radiotherapy equipment is determined based on the deviation between the projection to be detected and the reference projection. There is no need to manually install the film, such that the operation of detecting the installation deviation of the collimator is simplified. Therefore, the operation of adjusting the installation position of the collimator is simplified and the detection accuracy is improved. Meanwhile, the amount of radiation to installation persons is also reduced, and the impact on the health of the installation persons is further mitigated.

Figure 4:
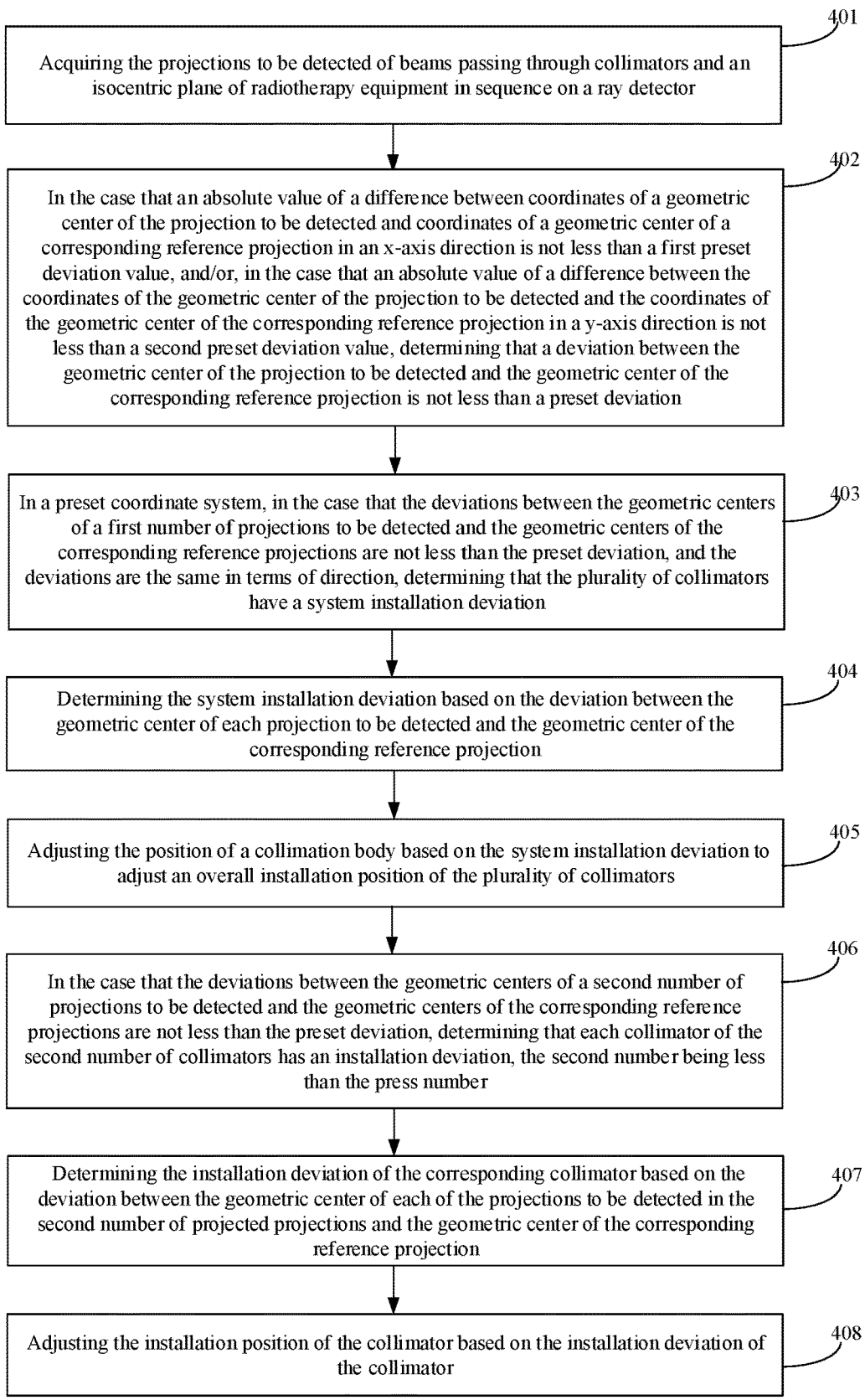
FIG. 4 is a flowchart of yet another method for detecting installation of a collimator of radiotherapy equipment according to an embodiment of the present disclosure.

Referring to FIG. 4, a flowchart of yet another method for detecting installation of a collimator of radiotherapy equipment according to an embodiment of the present disclosure is shown. The method may be configured for the processing component 01 in the implementation environment shown in FIG. 1. The method is employed to detect the installation deviation of the collimator of the radiotherapy equipment, wherein the radiotherapy equipment may be focusing radiotherapy equipment with a plurality of collimators. As shown in FIG. 4, the method may include the following steps:

In 401, the projections to be detected of the beams passing through the collimators and an isocentric plane of the radiotherapy equipment in sequence on the ray detector are acquired.

Figure 5:
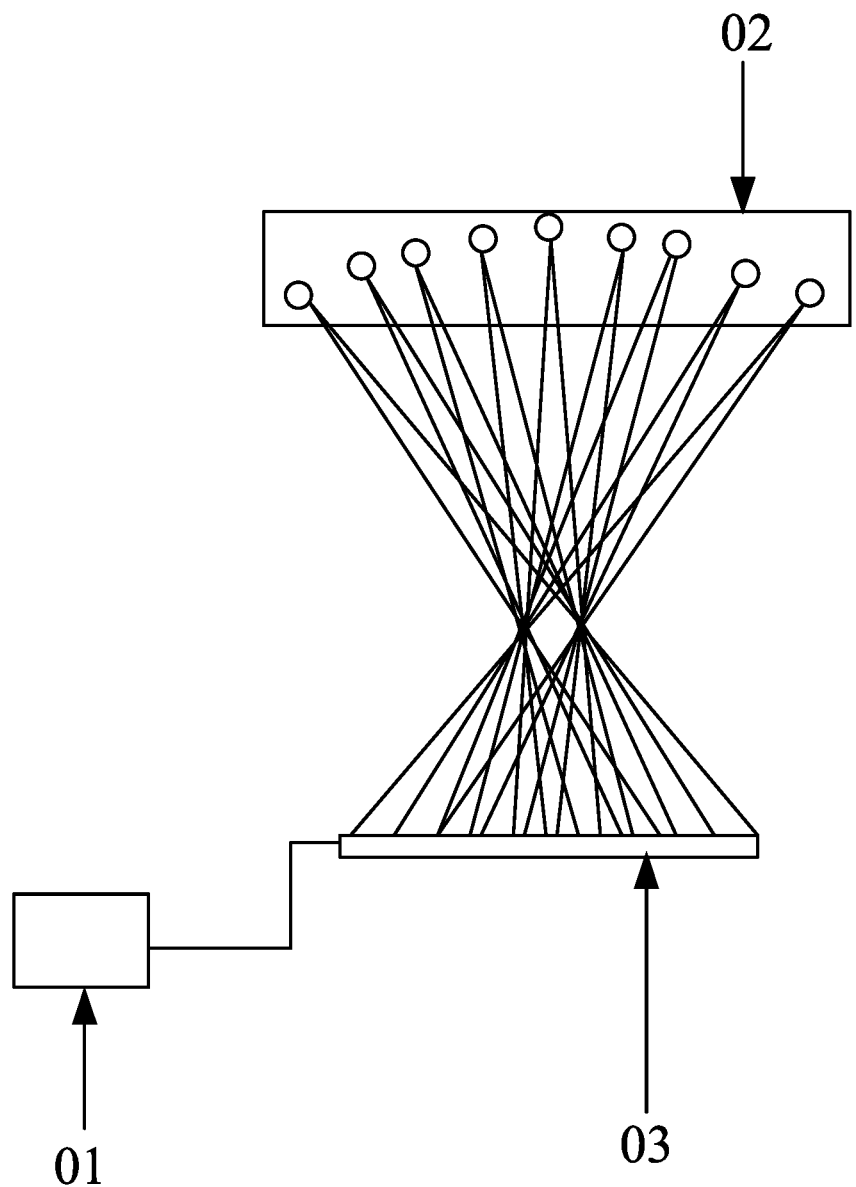
FIG. 5 is a schematic diagram of focusing radiotherapy equipment according to an embodiment of the present disclosure.

Exemplarily, the radiotherapy equipment is the focusing radiotherapy equipment with 18 collimators. The radiotherapy equipment includes 18 radiation sources. As shown in FIG. 5, the 18 radiation sources are divided into two groups, and the two groups of radiation sources are disposed side by side. The beams formed by the rays emitted from each group of radiation sources after passing through the corresponding collimators pass through the same focal point. Each beam passing through the collimator and the isocentric plane of the radiotherapy equipment in sequence forms one projection to be detected on the ray detector 03, and there are 18 projections to be detected in total. The processing component 01 acquires the projections to be detected of the beams passing through the collimators and the isocentric plane of the radiotherapy equipment in sequence on the ray detector.

In 402, in the case that an absolute value of a difference between coordinates of the geometric center of the projection to be detected and coordinates of the geometric center of the corresponding reference projection in an x-axis direction is not less than a first preset deviation value, and/or, in the case that an absolute value of a difference between the coordinates of the geometric center of the projection to be detected and the coordinates of the geometric center of the corresponding reference projection in a y-axis direction is not less than a second preset deviation value, it is determined that the deviation between the geometric center of the projection to be detected and the geometric center of the corresponding reference projection is not less than a preset deviation.

In the embodiment of the present disclosure, the deviation between the projection to be detected and the reference projection may be determined by comparing the coordinates of the geometric center of the projection to be detected with the coordinates of the geometric center of the corresponding reference projection in the preset coordinate system. The preset coordinate system is a two-dimensional coordinate system with an x-axis and a y-axis perpendicular to each other.

Optionally, the preset coordinate system may be established based on a detection surface of the ray detector, and the upper left corner of the detection surface is taken as an original point of the preset coordinate system. Exemplarily, the coordinates of the geometric center of one projection to be detected determined by the processing component may be expressed as (x1, y1), wherein x1 is the abscissa of the geometric center in the preset coordinate system, and y1 is the ordinate of the geometric center in the preset coordinate system.

That is, for each projection to be detected, in the case that the absolute value |x1−x2| of the difference between the abscissa x1 of the geometric center of the projection to be detected and the abscissa x2 of the geometric center of the corresponding reference projection is not less than the first preset deviation value, and/or, in the case that the absolute value |y1−y2| of the difference between the ordinate y1 of the geometric center of the projection to be detected and the ordinate y2 of the geometric center of the reference projection is not less than the second preset deviation value, the processing component determines that the deviation between the geometric center of the projection to be detected and the geometric center of the reference projection is not less than the preset deviation. The first preset deviation value and the second preset deviation value may be determined according to actual needs, which is not limited in the embodiment of the present disclosure.

Exemplarily, the coordinates of the geometric center of one projection to be detected determined by the processing component are (x1, y1), and the coordinates of the geometric center of the reference projection corresponding to such projection to be detected are (x2, y2). Assuming that |x1−x2| is greater than the first preset deviation value and |y1−y2| is greater than the second preset deviation value, then the processing component may determine that the deviation between the geometric center of the projection to be detected and the geometric center of the reference projection is not less than the preset deviation.

In 403, in the preset coordinate system, in the case that deviations between the geometric centers of a first number of projections to be detected and geometric centers of corresponding reference projections are not less than the preset deviation, and the deviations are the same in terms of direction, it is determined that the plurality of collimators have a system installation deviation.

The first number is greater than or equal to a preset number.

If the deviation between the geometric center of the projection to be detected and the geometric center of the corresponding reference projection is not less than the preset deviation, the deviation of the projection to be detected from the reference projection is greater. If the deviations are the same in terms of direction, all projections to be detected with a greater degree of deviation are deviated toward the same direction compared with the reference projection, for example, all deviated toward the lower right, all deviated toward the upper left, or the like. Then in the case that the deviations between the geometric centers of the first number of projections to be detected and the geometric centers of the corresponding reference projections are not less than the preset deviation, and the deviations are the same in terms of direction, the processing component may determine that all collimators have the system installation deviation, that is, the deviation between an overall installation position of all the collimators and a preset overall installation position is greater.

In addition, in the preset coordinate system, in the case that the deviations between the geometric centers of the first number of projections to be detected and the geometric centers of the corresponding reference projections are not less than the preset deviation, but the deviations are not the same in terms of direction, the processing component may determine that the plurality of collimators have no system installation deviation.

The preset number may be set based on the number of the collimators of the radiotherapy equipment. For example, when the radiotherapy equipment includes more collimators, the preset number may be set to be larger. When the radiotherapy equipment includes fewer collimators, the preset number may be set to be smaller. The embodiment of the present disclosure does not limit the value of the preset number.

Assuming that the reference projection is a preset projection of the collimator, as shown in FIG. 6, the projection to be detected is represented by a solid circle, and the reference projection is represented by a dashed circle, and there are 18 projections to be detected in total. Assuming that the preset number is 10, in the case that the deviations between the geometric centers of 11 projections to be detected and the geometric centers of the corresponding reference projections are not less than the preset deviation, and the deviations are the same in terms of direction, the processing component may determine that the 18 collimators have the system installation deviation, and step 404 and step 405 may be performed. As shown in FIG. 7, in the case that the deviations between the geometric centers of 3 projections to be detected and the geometric centers of the corresponding reference projections are not less than the preset deviation, and the deviations are the same in terms of direction, the processing component may determine that the 18 collimators have no system installation deviation, and step 406 to step 408 may be performed. Exemplarily, in the case that the deviations between the geometric centers of 11 projections to be detected and the geometric centers of the corresponding reference projections are not less than the preset deviation, but the deviations are not the same in terms of direction, the processing component may also determine that the 18 collimators have no system installation deviation.

For another example, the reference projection is the projection of a metal ball disposed in an isocenter of the radiotherapy equipment. As shown in FIG. 8, the projection to be detected is represented by a solid circle, and the reference projection is represented by a solid circle, and there are 18 projections to be detected in total. Assuming that the preset number is 10, in the case that the deviations between the geometric centers of four projections to be detected and the geometric centers of the corresponding reference projections are not less than the preset deviation, and the deviations are the same in terms of direction, the processing component may determine that the 18 collimators have no system installation deviation, and step 406 to step 408 may be performed.

In 404, the system installation deviation is determined based on the deviation between the geometric center of each projection to be detected and the geometric center of the corresponding reference projection.

Optionally, step 404 may include: determining a position offset value of all the projections to be detected based on the deviation between the geometric center of each projection to be detected and the geometric center of the corresponding reference projection; and determining the system installation deviation based on the position offset value of all the projections to be detected.

The position offset value L of all the projections to be detected satisfies:

$$L = \left( \frac{1}{N} \sum_{i=1}^{N} \Delta x_i, \frac{1}{N} \sum_{i=1}^{N} \Delta y_i \right),$$

wherein N is the number of the projections to be detected, $\Delta x_i$ is the difference between the coordinates of the geometric center of the $i(1 \leq i \leq N)^{th}$ projection to be detected and the geometric center of the corresponding reference projection in the x-axis direction, and $\Delta y_i$ is the difference between the coordinates of the geometric center of the $i^{th}$ projection to be detected and the coordinates of the geometric center of the corresponding reference projection in the y-axis direction.

Since the degree of deviation of an object projection position is usually greater than the degree of deviation of an actual installation position of the object, a product of the position deviation value L of all the projections to be detected and a conversion coefficient q (0<<1) may be used as the system installation deviation, that is the system installation deviation is $$\left( \frac{q}{N} \sum_{i=1}^{N} \Delta x_i, \frac{q}{N} \sum_{i=1}^{N} \Delta y_i \right).$$

In 405, the position of the collimation body is adjusted based on the system installation deviation to adjust the overall installation position of the plurality of collimators.

In this step, the processing component may adjust the overall installation position of all collimators simultaneously based on the magnitude and plus or minus of the system installation deviation determined in step 404, such that the number of the projections to be detected of which the deviations of the geometric centers are not less than the preset deviation and the deviations are the same in terms of direction is less than the preset number.

Exemplarily, the upper left corner of the detection surface of the ray detector is the original point of the preset coordinate system. Assuming that the position offset value of all the projections to be detected is L=(0.5, 0.8), and q=0.7, since 0.5 is greater than 0, and 0.8 is greater than 0, then all the projections to be detected with a large degree of deviation are deviated to the lower right, and then all collimators are moved to the upper left simultaneously based on the system installation deviation (0.5×0.7, 0.8×0.7).

In 406, in the case that deviations between geometric centers of a second number of projections to be detected and geometric centers of corresponding reference projections are not less than the preset deviation, it is determined that each collimator of the second number of collimators has an installation deviation.

The second number is less than the preset number.

In this step, in the case that the deviations between the geometric centers of the second number of projections to be detected and the geometric centers of the corresponding reference projections are not less than the preset deviation, the processing component may determine that each of the second number of collimators has the installation deviation.

Exemplarily, as shown in FIG. 7, the preset number is 10. In the case that the deviations between the geometric centers of three projections to be detected and the geometric centers of the corresponding reference projections are not less than the preset deviation, the processing component may determine that each of the corresponding three collimators has the installation deviation.

In 407, an installation deviation of a corresponding collimator is determined based on the deviation between the geometric center of each of the projections projection to be detected in the second number of projections and the geometric center of the corresponding reference projection.

Exemplarily, as shown in FIG. 7, the processing component determines that each of the 3 collimators has the installation deviation, the processing component may determine the installation deviation of the corresponding collimator based on the deviation ($\Delta x$, $\Delta y$) between the geometric center of each of the projections to be detected in the second number of projections to be detected and the geometric center of the corresponding reference projection, and further adjust the installation position of each collimator of the three collimators individually. $\Delta x$ is the difference between the coordinates of the geometric center of the projection to be detected and the coordinates of the geometric center of the corresponding reference projection in the x-axis direction, and $\Delta y$ is the difference between the coordinates of the geometric center of the projection to be detected and the coordinates of the geometric center of the corresponding reference projection in the y-axis direction. Similarly, since the degree of deviation of the object projection position is usually greater than the degree of deviation of the actual installation position of the object, the product of the deviation ($\Delta x$, $\Delta y$) between the geometric center of the projection to be detected and the geometric center of the corresponding reference projection and the conversion coefficient q (0<q<1) may be used as the installation deviation of the collimator.

In 408, the installation position of the collimator is adjusted based on the installation deviation of the collimator.

The processing component individually adjusts the installation position of each collimator in the second number of collimators based on the installation deviation of the collimator determined in step 407, such that the deviation between the geometric center of the projection to be detected and the geometric center of the corresponding reference projection is less than the preset deviation.

It should be noted that in the related art, a film is usually adopted to detect the installation deviation of the collimator, and the film is manually installed on the isocentric plane of the radiotherapy equipment. For example, the radiotherapy equipment includes nine radiation sources. The beams formed by the rays emitted from the nine radiation sources after passing through the corresponding collimators pass through the same focal point. The film is installed in a plane of the focal point. When the installation deviation of the collimator is detected, only the system installations deviation of all collimators may be detected. Specifically, when the projection center of the beam on the film is at a preset position, it is determined that all the collimators have no system installation deviation. When the projection center is not located at the preset position, it is determined that all the collimators have the system installation deviation, and the installation positions of all the collimators are further adjusted simultaneously. This detection mode cannot detect the installation deviation of a single collimator, and cannot determine whether the single collimator has an installation deviation.

However, in the embodiment of the present disclosure, through steps 406 to 408, whether the single collimator has the installation deviation may be determined. When the single collimator has the installation deviation, the installation deviation of the single collimator may be determined, and then the installation position of such collimator is adjusted based on the installation deviation of the single collimator. Compared with the related art, the method for detecting the installation of the collimator of the radiotherapy equipment according to the embodiments of the present disclosure can detect the installation deviation of a single collimator, such that the installation position of the collimator is more accurate, and a therapeutic effect of the radiotherapy equipment is further improved.

In summary, in the method for detecting the installation of the collimator of the radiotherapy equipment according to the embodiment of the present disclosure, the projection to be detected of the beam passing through the collimator and the isocentric plane of the radiotherapy equipment in sequence on the ray detector is acquired, the projection to be detected is compared with the reference projection, and the installation deviation of the collimator of the radiotherapy equipment is determined based on the deviation between the projection to be detected and the reference projection. There is no need to manually install the film, such that the operation of detecting the installation deviation of the collimator is simplified. Therefore, the operation of adjusting the installation position of the collimator is simplified and the detection accuracy is improved. Meanwhile, with the method, whether all the collimators have the system installation deviation can be determined, and whether a single collimator has the installation deviation can be determined, such that the installation position of the collimator is more accurate, and the therapeutic effect of the radiotherapy equipment is further improved. In addition, the amount of radiation to installation persons is also reduced, and the impact on the health of the installation persons is further mitigated.

Referring to FIG. 9, a flowchart of still a further method for detecting installation of a collimator of radiotherapy equipment according to an embodiment of the present disclosure is shown. The method may be configured for the processing component 01 in the implementation environment shown in FIG. 1. The method is employed to detect an installation stability of the collimator of the radiotherapy equipment. As shown in FIG. 9, the method includes the following steps:

In 901, projections to be detected of beams passing through the collimator and an isocentric plane of the radiotherapy equipment in sequence on a ray detector when a gantry of the radiotherapy equipment is rotated at different angles are acquired.

The isocentric plane refers to a plane passing through an isocenter and perpendicular to the connecting line between the radiotherapy equipment and the detector.

In 902, an installation stability of the collimator of the radiotherapy equipment is determined by comparing the projections to be detected acquired at the different rotation angles.

In summary, in the method for detecting the installation of the collimator of the radiotherapy equipment according to the embodiment of the present disclosure, the projections to be detected of the beams passing through the collimator and the isocentric plane of the radiotherapy equipment in sequence on the ray detector when the gantry of the radiotherapy equipment is at the different rotation angles are acquired, and the installation stability of the collimator of the radiotherapy equipment is determined by comparing the projections to be detected acquired at the different rotation angles. The operation of detecting the installation stability of the collimator is simplified, and the detection accuracy is higher.

Figure 10:
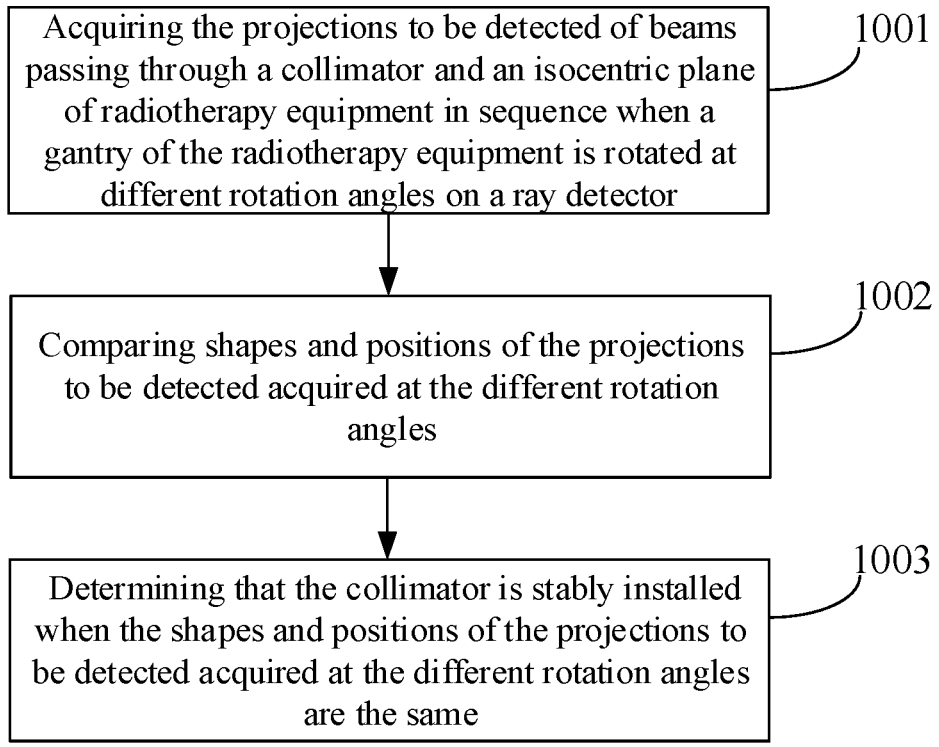
FIG. 10 is a flowchart of one additional method for detecting installation of a collimator of radiotherapy equipment according to an embodiment of the present disclosure.

Referring to FIG. 10, a flowchart of one additional method for detecting installation of a collimator of radiotherapy equipment according to an embodiment of the present disclosure is shown. The method may be configured for the processing component 01 in the implementation environment shown in FIG. 1. The method is employed to detect the installation stability of the collimator of the radiotherapy equipment. As shown in FIG. 10, the method may include:

In 1001, the projections to be detected of beams passing through the collimator and an isocentric plane of the radiotherapy equipment in sequence on a ray detector when a gantry of the radiotherapy equipment is rotated at different rotation angles are acquired.

The isocentric plane refers to a plane passing through an isocenter and perpendicular to the connecting line between the radiotherapy equipment and the detector.

In 1002, the shapes and positions of the projections to be detected acquired at the different rotation angles are compared.

Exemplarily, the radiotherapy equipment is conformal intensity-modulated radiotherapy equipment with a multi-leaf collimator. The processing component acquires the projection P1 to be detected of the beam passing through the collimator and the isocentric plane of the radiotherapy equipment in sequence on the ray detector when the gantry of the radiotherapy equipment is at a rotation angle a1, the projection P2 to be detected of the beam passing through the collimator and the isocentric plane of the radiotherapy equipment in sequence on the ray detector when the gantry of the radiotherapy equipment is at a rotation angle a2, and the projection P3 to be detected of the beam passing through the collimator and the isocentric plane of the radiotherapy equipment in sequence on the ray detector when the gantry of the radiotherapy equipment is at a rotation angle a3. The processing component compares the shapes and positions of the projected projection P 1, the projected projection P2, and the projected projection P3, and determines whether the collimator is stably installed based on a comparison result.

In 1003, when the shapes and positions of the projections to be detected acquired at the different rotation angles are the same, it is determined that the collimator is stably installed.

When the shapes and positions of the projections to be detected acquired at the different rotation angles are the same, the processing component may determine that the collimator is stably installed. When at least one of the shapes and positions of the projections to be detected acquired at the different rotation angles is different, it is determined that the collimator is unstably installed.

In addition, when the method for detecting the installation of the collimator of the radiotherapy equipment according to the embodiment of the present disclosure is adopted to detect the installation stability of the collimator of the radiotherapy equipment, coordinates of the geometric centers of the projections to be detected when the gantry of the radiotherapy equipment is at the different rotation angles may also be acquired, and then whether the corresponding collimator is stably installed is determined based on the multiple groups of coordinates of the geometric centers of the projections to be detected.

Optionally, a variance of the coordinates of the geometric centers of the projections to be detected at all angles may be calculated, and then whether the variance is greater than a preset variance is determined. When the variance is not greater than the preset variance, it may be determined that the corresponding collimator is stably installed.

Generally, the variance indicates the degree of deviation of a group of data from an average value of such group of data. The smaller the variance is, the smaller the fluctuation of the group of data is and the better the stability is. In the embodiment of the present disclosure, the variance indicates the degree of deviation of the multiple groups of coordinates of the geometric centers of the projections to be detected from the average value of such multiple groups of coordinates. If the variance is smaller, the fluctuation of the coordinates of the geometric centers of the projections to be detected is smaller, which indicates better stability, and further indicates that the installation stability of the corresponding collimator is better.

Exemplarily, for the certain projection P1 to be detected, when the gantry of the radiotherapy equipment rotates to the angle a1, the processing component acquires coordinates (x1, y1) of the geometric center of the projection P1 to be detected. When the gantry rotates to the angle a2 (a2>a1), the processing component acquires coordinates (x2, y2) of the geometric center of the projection P1 to be detected. When the gantry rotates to the angle a3 (a3>a2), the processing component acquires coordinates (x3, y3) of the geometric center of the projection P1 to be detected. When the gantry rotates to the angle a4 (a4>a3), the processing component acquires coordinates (x4, y4) of the geometric center of the projection P1 to be detected. Then, the processing component calculates the average value $$M1 = \frac{x1 + x2 + x3 + x4}{4}$$

of the abscissas and the average value $$M2 = \frac{y1 + y2 + y3 + y4}{4}$$

of the ordinates of the geometric center of the projection P1 to be detected. Afterwards, the processing component calculates the variance $$S^2 = \frac{(M1-x1)^2 + (M1-x2)^2 + (M1-x3)^2 + (M1-x4)^2}{4} + \frac{(M1-y1)^2 + (M1-y2)^2 + (M1-y3)^2 + (M1-y4)^2}{4}$$

of the coordinates of the geometric center of the projection P1 to be detected at different angles. When the variance $S^2$ is not greater than the preset variance, it can be determined that the corresponding collimator is stably installed.

In summary, in the method for detecting the installation of the collimator of the radiotherapy equipment according to the embodiment of the present disclosure, the projections to be detected of the beams of the gantry of the radiotherapy equipment passing through the collimator and the isocentric plane of the radiotherapy equipment in sequence at the different rotation angles on the ray detector are acquired, and the installation stability of the collimator of the radiotherapy equipment is determined by comparing the projections to be detected acquired at the different rotation angles. The operation of detecting the installation stability of the collimator is simplified, and the detection accuracy is higher.

It should be noted that in the method for detecting the installation of the collimator of the radiotherapy equipment according to the embodiment of the present disclosure, the order of the steps may be appropriately adjusted, and the steps may be correspondingly increased or decreased as needed. Various methods which can be easily expected by any person skilled in the art within the technical scope of the present disclosure should be covered by the protection scope of the present disclosure, which are thus not repeated herein.

Figure 11:
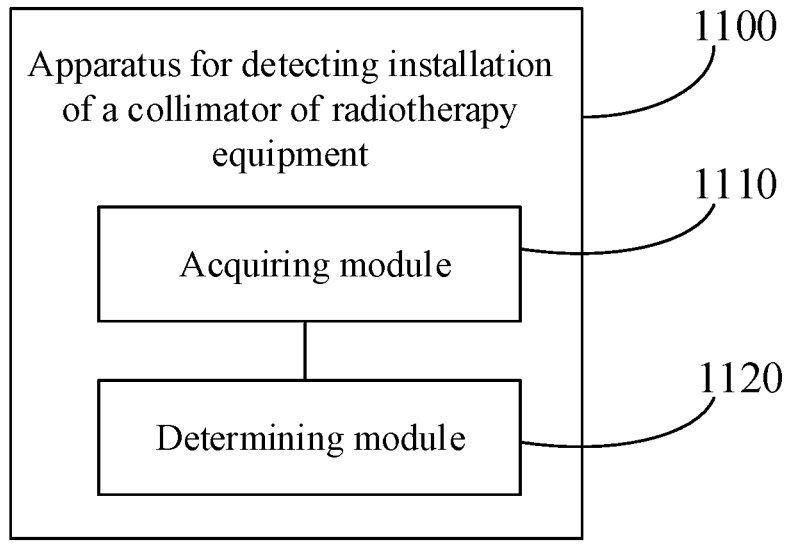
FIG. 11 is a schematic structural diagram of a device for detecting installation of a collimator of radiotherapy equipment according to an embodiment of the present disclosure.

An embodiment of the present disclosure also provides an apparatus for detecting installation of a collimator of radiotherapy equipment. The apparatus is configured for the processing component 01 in the implementation environment shown in FIG. 1. The apparatus is configured to detect the installation deviation of the collimator of the radiotherapy equipment. As shown in FIG. 11, the apparatus 1100 includes:

an acquiring module 1110, configured to acquire a projection to be detected of a beam passing through the collimator and an isocentric plane of the radiotherapy equipment in sequence on a ray detector; and a determining module 1120, configured to compare the projection to be detected with a reference projection, and determine an installation deviation of the collimator of the radiotherapy equipment based on a deviation between the projection to be detected and the reference projection.

Optionally, the determining module 1120 is configured to respectively determine a geometric center of the projection to be detected and a geometric center of the reference projection; and determine the installation deviation of the collimator of the radiotherapy equipment based on a deviation between the geometric center of the projection to be detected and the geometric center of the reference projection.

Optionally, the reference projection is a preset projection of the collimator or a projection of a metal ball disposed in an isocenter of the radiotherapy equipment.

Optionally, the radiotherapy equipment is focusing radiotherapy equipment with a plurality of collimators, and the determining module 1120 is configured to, in a preset coordinate system, when deviations between geometric centers of a first number of projections to be detected and geometric centers of corresponding reference projections are not less than a preset deviation, and the deviations are the same in terms of direction, determine that the plurality of collimators have a system installation deviation, the first number being greater than or equal to a preset number; and determine the system installation deviation based on the deviation between the geometric center of each of the projections to be detected and the geometric center of the corresponding reference projection.

Optionally, the determining module 1120 is further configured to, when deviations between geometric centers of a second number of projections to be detected and geometric centers of corresponding reference projections are not less than the preset deviation, determine that each collimator of the second number of collimators has an installation deviation, the second number being less than the preset number; and determine the installation deviation of the corresponding collimator based on the deviation between the geometric center of each of the projections to be detected in the second number of projections to be detected and the geometric center of the corresponding reference projection.

Optionally, the preset coordinate system is a two-dimensional coordinate system having an x-axis and a y-axis perpendicular to each other; and the apparatus 1100 may further include:

a processing module, configured to, in the case that an absolute value of a difference between coordinates of the geometric center of the projection to be detected and coordinates of the geometric center of the corresponding reference projection in an x-axis direction is not less than a first preset deviation value, and/or, in the case that an absolute value of a difference between the coordinates of the geometric center of the projection to be detected and the coordinates of the geometric center of the corresponding reference projection in a y-axis direction is not less than a second preset deviation value, determine that the deviation between the geometric center of the projection to be detected and the geometric center of the corresponding reference projection is not less than the preset deviation.

Optionally, a plurality of collimators are disposed in a collimation body; and the apparatus 1100 may further include:

an adjustment module, configured to adjust, based on the system installation deviation, a position of the collimation body to adjust an overall installation position of the plurality of collimators; and adjust an installation position of the collimator based on the installation deviation of the collimator.

In summary, in the apparatus for detecting the installation of the collimator of the radiotherapy equipment according to the embodiment of the present disclosure, the projection to be detected of the beam passing through the collimator and the isocentric plane of the radiotherapy equipment in sequence on the ray detector is acquired, the projection to be detected is compared with the reference projection, and the installation deviation of the collimator of the radiotherapy equipment is determined based on the deviation between the projection to be detected and the reference projection. There is no need to manually install the film, such that the operation of detecting the installation deviation of the collimator is simplified. Therefore, the operation of adjusting the installation position of the collimator is simplified and the detection accuracy is improved. Meanwhile, with the device, whether all the collimators have the system installation deviation can be determined, and whether a single collimator has the installation deviation can be determined, such that the installation position of the collimator is more accurate, and a therapeutic effect of the radiotherapy equipment is further improved. In addition, the amount of radiation to installation persons is also reduced, and the impact on the health of the installation persons is further mitigated.

Figure 12:
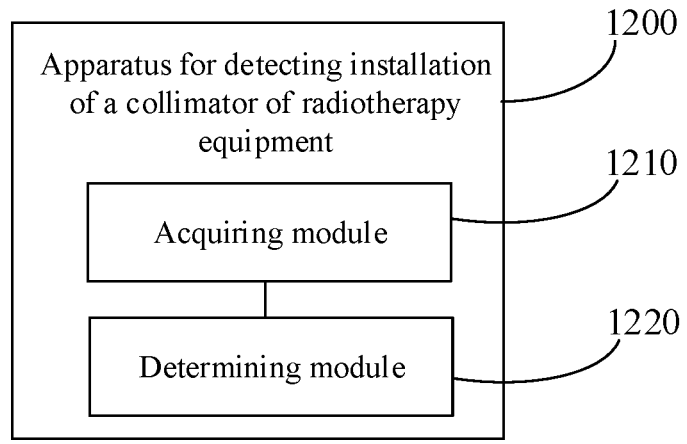
FIG. 12 is a schematic structural diagram of another device for detecting installation of a collimator of radiotherapy equipment according to an embodiment of the present disclosure.

An embodiment of the present disclosure also provides another apparatus for detecting installation of a collimator of radiotherapy equipment. The apparatus is configured for the processing component 01 in the implementation environment shown in FIG. 1. The apparatus is configured to detect the installation stability of the collimator of the radiotherapy equipment. As shown in FIG. 12, the apparatus 1200 includes:

an acquiring module 1210, configured to acquire projections to be detected of beams passing through the collimator and an isocentric plane of the radiotherapy equipment when a gantry of the radiotherapy equipment is rotated at different rotation angles on a ray detector; and a determining module 1220, configured to determine an installation stability of the collimator of the radiotherapy equipment by comparing the projections to be detected acquired at the different rotation angles.

Optionally, the determining module 1220 is configured to compare shapes and positions of the projections to be detected acquired at the different rotation angles, and determine that the collimator is stably installed in the case that the shapes and positions of the projections to be detected acquired at the different rotation angles are the same.

In summary, in the apparatus for detecting the installation of the collimator of the radiotherapy equipment according to the embodiment of the present disclosure, the projections to be detected of the beams of the gantry of the radiotherapy equipment passing through the collimator and the isocentric plane of the radiotherapy equipment in sequence at the different rotation angles on the ray detector are acquired, and the installation stability of the collimator of the radiotherapy equipment is determined by comparing the projections to be detected acquired at the different rotation angles. The operation of detecting the installation stability of the collimator is simplified, and the detection accuracy is higher.

Figure 13:
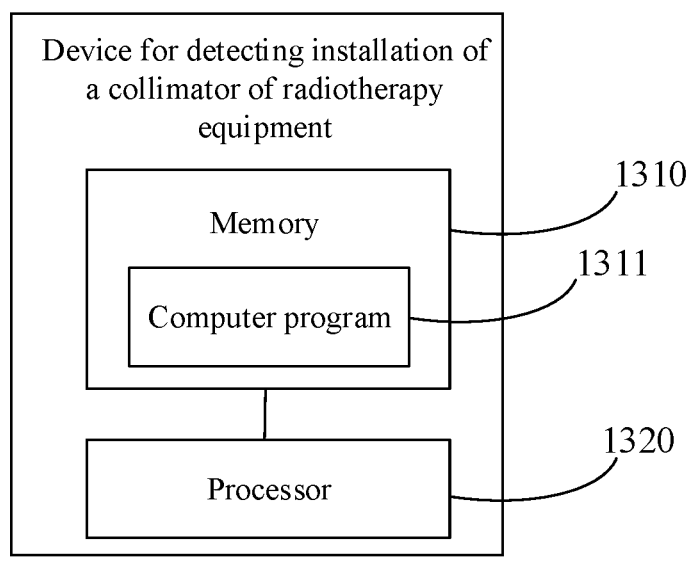
FIG. 13 is a schematic structural diagram of yet another device for detecting installation of a collimator of radiotherapy equipment according to an embodiment of the present disclosure.

An embodiment of the present disclosure also provides a device for detecting installation of a collimator of radiotherapy equipment. As shown in FIG. 13, the device includes a memory 1310, a processor 1320, and a computer program 1311 stored in the memory 1310 and capable of running on the processor 1320. The processor 1320, when executing the computer program, is caused to perform the steps of the method for detecting installation of a collimator of radiotherapy equipment as shown in FIG. 2, FIG. 3, or FIG. 4.

An embodiment of the present disclosure also provides a computer-readable storage medium, which is a non-volatile readable storage medium. The computer-readable storage medium stores a computer program. The computer program, when executed by a processor, causes the processor to perform the steps of the method for detecting installation of a collimator of radiotherapy equipment as shown in FIG. 2, FIG. 3, or FIG. 4.

An embodiment of the present disclosure also provides a computer program product. The computer program product stores instructions therein. The computer program product, when running on a computer, causes the computer to perform the steps of the method for detecting installation of a collimator of radiotherapy equipment as shown in FIG. 2, FIG. 3, or FIG. 4.

An embodiment of the present disclosure also provides a chip. The chip includes a programmable logic circuit and/or program instructions. The chip, when running, is configured to perform the steps of the method for detecting installation of a collimator of radiotherapy equipment as shown in FIG. 2, FIG. 3, or FIG. 4.

An embodiment of the present disclosure also provides a device for detecting installation of a collimator of radiotherapy equipment. As shown in FIG. 13, the device includes a memory, a processor, and a computer program stored in the memory and capable of running on the processor. The processor, when executing the computer program, is caused to perform the steps of the method for detecting installation of a collimator of radiotherapy equipment as shown in FIG. 9 or FIG. 10.

An embodiment of the present disclosure also provides a computer-readable storage medium, which is a non-volatile readable storage medium. The computer-readable storage medium stores a computer program. The computer program, when executed by a processor, causes the processor to perform the steps of the method for detecting the installation of the collimator of the radiotherapy equipment as shown in FIG. 9 or FIG. 10.

An embodiment of the present disclosure also provides a computer program product. The computer program product stores instructions therein. The computer program, when running on a computer, causes the computer program to perform the steps of the method for detecting the installation of the collimator of the radiotherapy equipment as shown in FIG. 9 or FIG. 10.

An embodiment of the present disclosure also provides a chip. The chip includes a programmable logic circuit and/or program instructions. The chip, when running, is configured to perform the steps of the method for detecting the installation of the collimator of the radiotherapy equipment as shown in FIG. 9 or FIG. 10.

An embodiment of the present disclosure also provides a system for detecting installation of a collimator of radiotherapy equipment, which includes the radiotherapy equipment, a ray detector, and a processing component.

The processing component includes the apparatus for detecting the installation of the collimator of the radiotherapy equipment as shown in FIG. 11.

A beam passing through the collimator and an isocentric plane of the radiotherapy equipment in sequence forms a projection to be detected on the ray detector.

Optionally, the processing component further includes the apparatus for detecting the installation of the collimator of the radiotherapy equipment as shown in FIG. 12.

Persons of ordinary skill in the art can understand that all or part of the steps described in the above embodiments can be performed by hardware, or by relevant hardware instructed by programs stored in a computer-readable storage medium, such as a read-only memory, a disk, or a CD.

Described above are merely exemplary embodiments of the present disclosure, and are not intended to limit the present disclosure. Within the spirit and principles of the disclosure, any modifications, equivalent substitutions, improvements, and the like are within the protection scope of the present disclosure.

What is claimed is:

1. A method for detecting installation of a collimator of radiotherapy equipment, comprising:
    acquiring a projection to be detected of a beam passing through the collimator and an isocentric plane of the radiotherapy equipment in sequence on a ray detector; and
    comparing the projection to be detected with a reference projection, and determining an installation deviation of the collimator of the radiotherapy equipment based on a deviation between the projection to be detected and the reference projection.

2. The method according to claim 1, wherein said comparing the projection to be detected with the reference projection, and determining the installation deviation of the collimator of the radiotherapy equipment based on the deviation between the projection to be detected and the reference projection comprises:
    respectively determining a geometric center of the projection to be detected and a geometric center of the reference projection; and
    determining the installation deviation of the collimator of the radiotherapy equipment based on a deviation between the geometric center of the projection to be detected and the geometric center of the reference projection.

3. The method according to claim 1, wherein the reference projection is a preset projection of the collimator or a projection of a metal ball disposed in an isocenter of the radiotherapy equipment.

4. The method according to claim 1, wherein: the radiotherapy equipment is focusing radiotherapy equipment with a plurality of collimators; and said comparing the projection to be detected with the reference projection, and determining the installation deviation of the collimator of the radiotherapy equipment based on the deviation between the projection to be detected and the reference projection comprises:
    in a preset coordinate system, in response to deviations between geometric centers of a first number of projections to be detected and geometric centers of corresponding reference projections being not less than a preset deviation, and the deviations being same in terms of direction, determining that the plurality of collimators have a system installation deviation, the first number being greater than or equal to a preset number; and
    determining the system installation deviation based on the deviation between the geometric center of each of the projections to be detected and the geometric center of the corresponding reference projection.

5. The method according to claim 4, wherein after said determining the system installation deviation, the method further comprises:
    in response to deviations between geometric centers of a second number of projections to be detected and geometric centers of corresponding reference projections being not less than the preset deviation, determining that each collimator of the second number of collimators has an installation deviation, the second number being less than the preset number; and
    determining an installation deviation of a corresponding collimator based on the deviation between the geometric center of each of the projections to be detected in the second number of projections to be detected and the geometric center of the corresponding reference projection.

6. The method according to claim 4, wherein, the preset coordinate system is a two-dimensional coordinate system having an x-axis and a y-axis perpendicular to each other; and after said acquiring the projection to be detected of the beam passing through the collimator and the isocentric plane of the radiotherapy equipment in sequence on the ray detector, the method further comprises:
    in response to an absolute value of a difference between coordinates of the geometric center of the projection to be detected and coordinates of the geometric center of the corresponding reference projection in an x-axis direction being not less than a first preset deviation value, and/or, in response to an absolute value of a difference between the coordinates of the geometric center of the projection to be detected and the coordinates of the geometric center of the corresponding reference projection in a y-axis direction being not less than a second preset deviation value, determining that the deviation between the geometric center of the projection to be detected and the geometric center of the corresponding reference projection is not less than the preset deviation.

7. The method according to claim 5, wherein the plurality of collimators are disposed in a collimation body; and after said determining the system installation deviation, the method further comprises:

adjusting an overall installation position of the plurality of collimators by adjusting a position of the collimation body based on the system installation deviation; and after said determining the installation deviation of the corresponding collimator, the method further comprises:

adjusting an installation position of the collimator based on the installation deviation of the collimator.

8. A non-volatile computer-readable storage medium storing a computer program, wherein the computer program, when executed by a processor, causes the processor to perform the steps of the method as defined in claim 1.

9. A computer program product storing instructions, wherein the computer program product, when running on a computer, causes the computer to perform the steps of the method as defined in claim 1.

10. A method for detecting installation of a collimator of radiotherapy equipment, comprising:

acquiring projections to be detected of beams passing through the collimator and an isocentric plane of the radiotherapy equipment in sequence when a gantry of the radiotherapy equipment is rotated at different rotation angles on a ray detector; and determining an installation stability of the collimator of the radiotherapy equipment by comparing the projections to be detected acquired at the different rotation angles.

11. The method according to claim 10, wherein said determining the installation stability of the collimator of the radiotherapy equipment by said comparing the projections to be detected acquired at the different rotation angles comprises:

comparing shapes and positions of the projections to be detected acquired at the different rotation angles; and determining that the collimator is stably installed in response to the shapes and the positions of the projections to be detected acquired at the different rotation angles being same.

12. A non-volatile computer-readable storage medium storing a computer program, wherein the computer program, when executed by a processor, causes the processor to perform the steps of the method as defined in claim 10.

13. A device for detecting installation of a collimator of radiotherapy equipment, comprising:

a memory, a processor, and a computer program stored in the memory and capable of running on the processor; wherein the processor, when executing the computer program, is caused to perform a method for detecting the installation of the collimator of the radiotherapy equipment, the method comprising:

acquiring a projection to be detected of a beam passing through the collimator and an isocentric plane of the radiotherapy equipment in sequence on a ray detector; and comparing the projection to be detected with a reference projection, and determining an installation deviation of the collimator of the radiotherapy equipment based on a deviation between the projection to be detected and the reference projection.

14. The device according to claim 13, wherein said comparing the projection to be detected with the reference projection, and determining the installation deviation of the collimator of the radiotherapy equipment based on the deviation between the projection to be detected and the reference projection comprises:

respectively determining a geometric center of the projection to be detected and a geometric center of the reference projection; and determining the installation deviation of the collimator of the radiotherapy equipment based on a deviation between the geometric center of the projection to be detected and the geometric center of the reference projection.

15. The device according to claim 13, wherein the reference projection is a preset projection of the collimator or a projection of a metal ball disposed in an isocenter of the radiotherapy equipment.

16. The device according to claim 13, wherein: the radiotherapy equipment is focusing radiotherapy equipment with a plurality of collimators; and said comparing the projection to be detected with the reference projection, and determining the installation deviation of the collimator of the radiotherapy equipment based on the deviation between the projection to be detected and the reference projection comprises:

in a preset coordinate system, in response to deviations between geometric centers of a first number of projections to be detected and geometric centers of corresponding reference projections being not less than a preset deviation, and the deviations are same in terms of direction, determining that the plurality of collimators have a system installation deviation, the first number being greater than or equal to a preset number; and determining the system installation deviation based on the deviation between the geometric center of each of the projections to be detected and the geometric center of the corresponding reference projection.

17. The device according to claim 16, wherein after said determining the system installation deviation, the method further comprises:

in response to deviations between geometric centers of a second number of projections to be detected and geometric centers of corresponding reference projections being not less than the preset deviation, determining that each collimator of the second number of collimators has an installation deviation, the second number being less than the preset number; and determining an installation deviation of a corresponding collimator based on the deviation between the geometric center of each of the projections to be detected in the second number of projections to be detected and the geometric center of the corresponding reference projection.

18. The device according to claim 16, wherein: the preset coordinate system is a two-dimensional coordinate system having an x-axis and a y-axis perpendicular to each other; and after said acquiring the projection to be detected of the beam passing through the collimator and the isocentric plane of the radiotherapy equipment in sequence on the ray detector, the method further comprises:

in response to an absolute value of a difference between coordinates of the geometric center of the projection to be detected and coordinates of the geometric center of the corresponding reference projection in an x-axis direction being not less than a first preset deviation value, and/or, in response to an absolute value of a difference between the coordinates of the geometric center of the projection to be detected and the coordinates of the geometric center of the corresponding reference projection in a y-axis direction being not less than a second preset deviation value, determining that the deviation between the geometric center of the projection to be detected and the geometric center of the corresponding reference projection is not less than the preset deviation.

19. The device according to claim 17, wherein: the plurality of collimators are disposed in a collimation body; and after said determining the system installation deviation, the method further comprises:

adjusting an overall installation position of the plurality of collimators by adjusting a position of the collimation body based on the system installation deviation; and after said determining the installation deviation of the corresponding collimator, the method further comprises:

adjusting an installation position of the collimator based on the installation deviation of the collimator.

20. A system for detecting installation of a collimator of radiotherapy equipment, comprising: the radiotherapy equipment, a ray detector, and a processing component; wherein:

the processing component comprises the device for detecting the installation of the collimator of the radiotherapy equipment as defined in claim 13; and a beam passing through the collimator and an isocentric plane of the radiotherapy equipment in sequence forms a projection to be detected on the ray detector.

* * * * *